United States Patent [19]
Gunawardana et al.

[11] Patent Number: 5,863,773
[45] Date of Patent: Jan. 26, 1999

[54] ANTIFUNGAL CORYNECANDIN

[75] Inventors: Geewananda P. Gunawardana, Libertyville; David Frost, Deerfield; Marianna Jackson, Waukegan; James P. Karwowski, Mundelein, all of Ill.; Ronald R. Rasmussen, Burlington, Wis.

[73] Assignee: Abbott Laboratories, Abbott Park, Ill.

[21] Appl. No.: 940,513

[22] Filed: Sep. 30, 1997

[51] Int. Cl.$^6$ ................ C12P 1/02; C12P 17/16; A61K 31/35; C07D 315/00
[52] U.S. Cl. .......... 435/118; 435/171; 514/460; 549/415
[58] Field of Search ............ 514/460; 549/415; 435/118, 171

[56] References Cited

U.S. PATENT DOCUMENTS 5,585,251 12/1996 Alder et al. .

OTHER PUBLICATIONS

Journal of Antibiotics, vol. 38. No. 4 (1985), pp. 455–459, Komori et al., "Chaetiacandin, A Novel Papulacandin I. Fermentation. Isolation and Characterization".

Journal of Antibiotics, vol. 33, No. 9 (1980), pp. 967–978, Traxier et al., "Papulacandins, A New Family of Antibiotics with Antifungal Activity: Structures of Papulacandins A. B. C and D".

Journal of Antibiotics, vol. 38. No. 4 (1985), pp. 544–546, Komori et al., "Chaetiacandin, A Novel Papulacandin II. Structure Determination".

*Primary Examiner*—Johann Richter
*Assistant Examiner*—Taofiq A. Solola
*Attorney, Agent, or Firm*—Mona Anand

[57] ABSTRACT

Disclosed are novel antifungal agents having the formula:

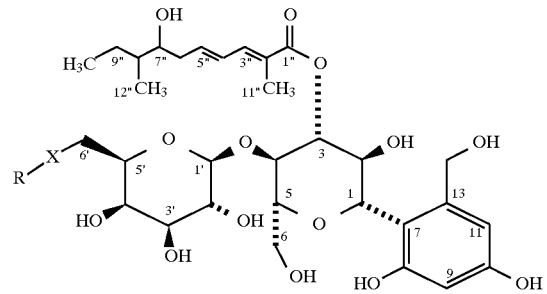

as well as a pharmaceutically acceptable salt, ester of prodrug thereof, wherein R is:

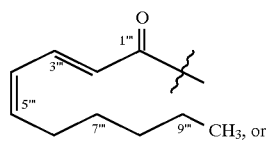

—C(O)—$R_1$ wherein $R_1$ is alkyl, alkenyl, aryl, arylalkenyl, aryl-aryl-, arylalkoxy-aryl-, aryl-aryl-aryl-, arylkoxy-aryl-aryl-, or

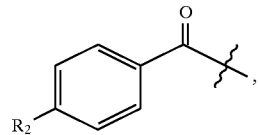

wherein $R_2$ is alkylamino, dialkylamino, (heterocyclic) alkyl, aryl, or arylalkyl; and X is O, NH, or $NR_3$ wherein $R_3$ is alkyl or aryl. Also disclosed are pharmaceutical compositions comprising a compound of the invention in combination with a pharmaceutically acceptable carrier; and a process for preparing the compounds of the invention.

10 Claims, 2 Drawing Sheets

ANTIFUNGAL CORYNECANDIN

TECHNICAL FIELD

The present invention relates to novel fungal isolates of potential medicinal value as well as chemically modified derivatives thereof. More particularly, the invention relates to a novel antifungal glycolipid isolated from cultures of the *Coryneum modonium* species, herein designated "corynecandin", as well as chemically modified derivatives thereof which possess antifungal activity, as well as to methods and cultures of microorganisms useful for the preparation of corynecandins or corynecandin analogs, pharmaceutical compositions containing such compounds, and the use thereof in treating fungal infections.

BACKGROUND OF THE INVENTION

The compounds of the present invention are related to those of the papulacandin class, described in *J. Antibiotics* 33(9):967–977 (1980). Papulacandins include BE-29602, disclosed in a published Japanese patent application of Banyu Pharmaceutical Co. (No. JP05170784-A, published Jul. 9, 1993) and isolated from a Fusarium species of fungus, chaetiacandin, disclosed in *J. Antibiotics* 38(4):455–459 (1985) and *J. Antibiotics* 38(4):544–546 (1985), and fusacandins, disclosed in U.S. Pat. No. 5,585,251, issued Dec. 17, 1996.

SUMMARY OF THE INVENTION

It has now been found that novel antifungal agents of the corynecandin class, herein designated "corynecandins", can be obtained by the fermentation of certain cultures belonging to the fungal species *Coryneum modonium* strain AB 2020T-223 (NRRL 25349).

Accordingly, in one aspect of the present invention are disclosed compounds of the formula:

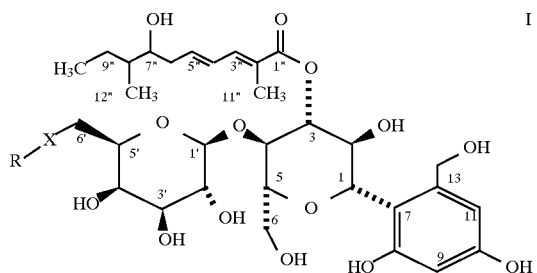

as well as a pharmaceutically acceptable salt, ester of prodrug thereof. In the above formula:

R is:

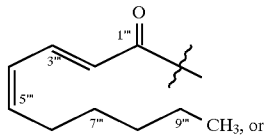

—C(O)—$R_1$ wherein $R_1$ is alkyl, alkenyl, aryl, arylalkenyl, aryl-aryl-, arylalkoxy-aryl-, aryl-aryl-aryl-, arylkoxy-aryl-aryl-, or

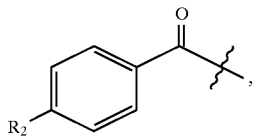

wherein $R_2$ is alkylamino, dialkylamino, (heterocyclic) alkyl, aryl, or arylalkyl; and X is O, NH, or $NR_3$ wherein $R_3$ is alkyl or aryl.

In another aspect, the present invention is a pharmaceutical composition which comprises a compound of the invention in combination with a pharmaceutically acceptable carrier.

In yet another aspect, the present invention is a method of suppressing or inhibiting a fungal infection in a patient in need of such treatment, comprising administering to the patient a therapeutically effective amount of a compound of the invention.

In still yet another aspect, the present invention is a process for preparing the compounds of the invention which comprises the steps of (a) culturing a microorganism having substantially all the characteristics of *Coryneum modonium* species AB 2020T-223 under suitable conditions in a fermentation medium containing assimilable sources of carbon and nitrogen; (b) allowing the desired compound to accumulate in the fermentation medium; and (c) isolating the compound from the fermentation medium. Preferably, the microorganism to be cultured is *Coryneum modonium* strain NRRL 25349 or a mutant or derivative thereof. Synthetic processes for preparing other compounds of the invention are described below.

Similarly, in still additional aspect, the present invention is a biologically pure culture of a microorganism capable of producing the compounds of the invention, namely, a microorganism having substantially all the characteristics of *Coryneum modonium* species. strain AB 2020T-223. Preferably, the microorganism is *Coryneum modonium* strain NRRL 25349 or a mutant or derivative thereof.

BRIEF DESCRIPTION OF THE DRAWINGS

The present invention will be better understood in connection with the following figures, in which.

DETAILED DESCRIPTION OF THE INVENTION

Definitions

Figure 1:
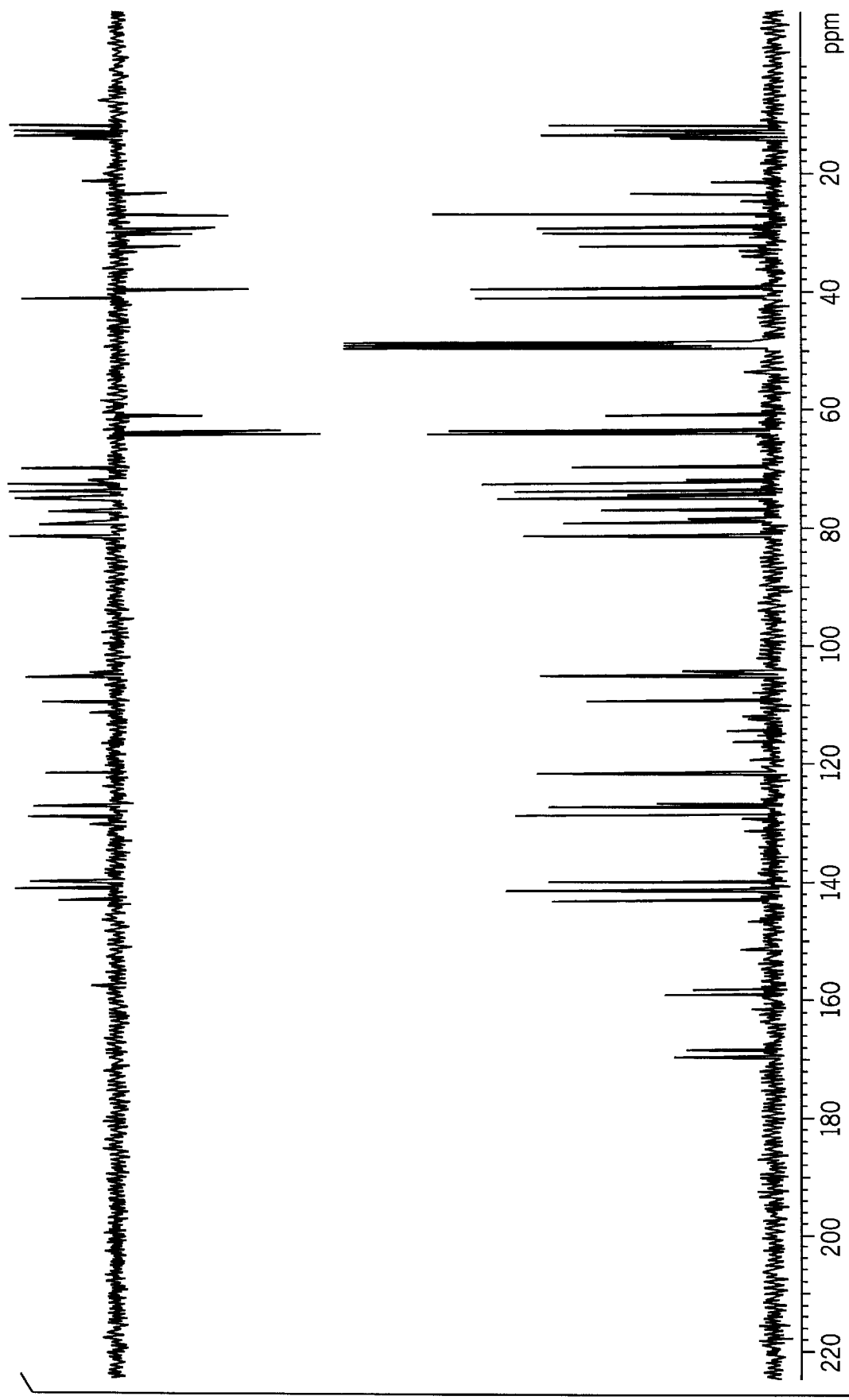
FIG. 1 is a proton nuclear magnetic resonance (NMR) spectrum of Corynecandin in $CD_3OD$.
Figure 2:
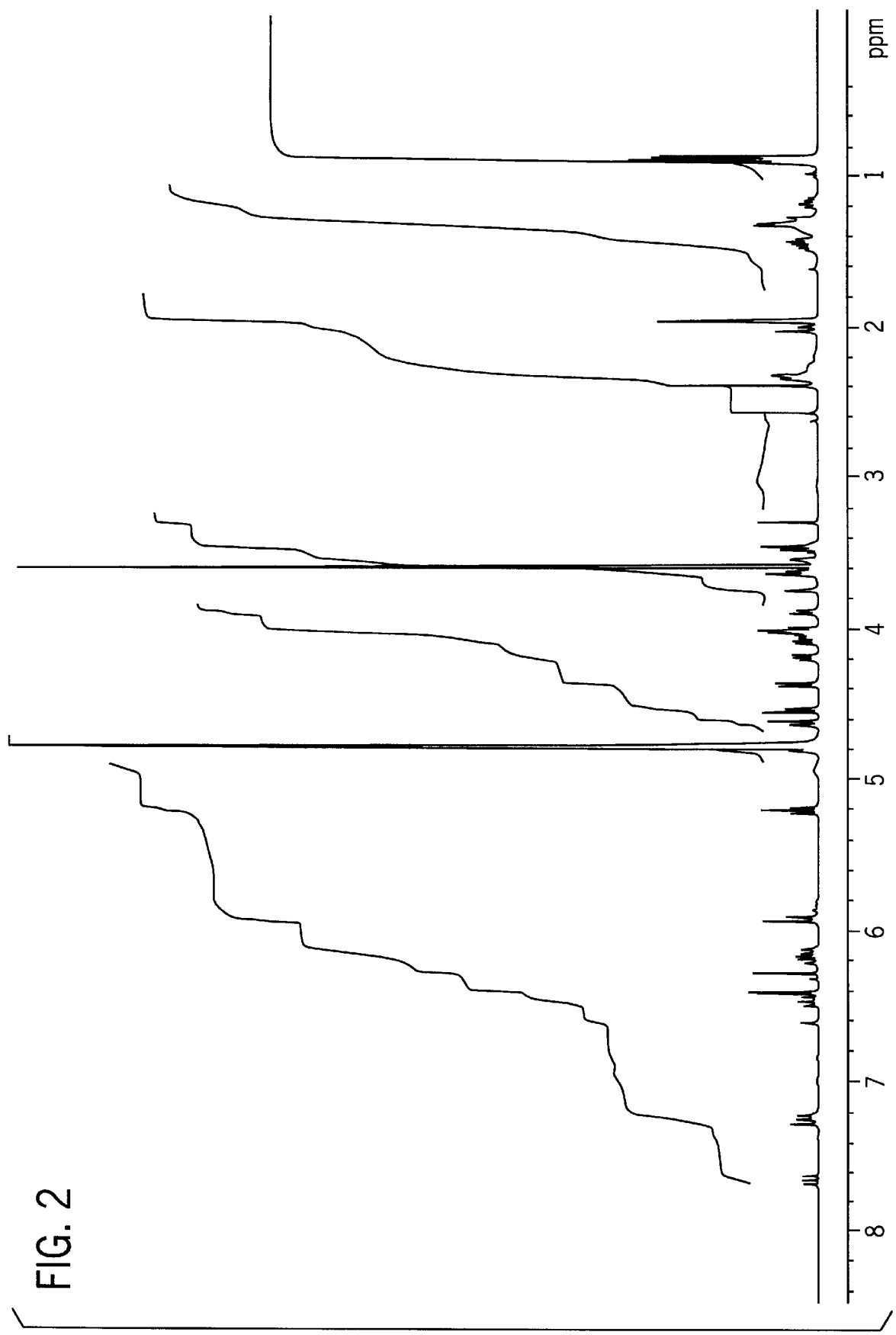
FIG. 2 is a carbon NMR spectrum of Corynecandin in $CD_3OD$.

As used throughout this specification and in the appended claims, the following terms have the meanings specified:

The term "mutant or derivative" as used herein refers to fungal strains which are obtained by mutagenization or genetic modification of *Coryneum modonium* strain NRRL 25349 by techniques readily known in the art.

The term "biologically pure" as used herein refers to fungal cultures which are substantially free from biologically active contaminants.

The terms "loweralkyl" or "alkyl" as used herein refer to straight or branched chain alkyl radicals containing from 1 to 20 carbon atoms, sometimes represented as $C_n$–$C_m$-alkyl where n and m respectively represent the minimum and maximum number of carbon atoms in the alkyl radical. Examples of lower alkyl include, but are not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkylamino" as used herein refers to $R_6NH-$ wherein $R_6$ is a loweralkyl group, for example, ethylamino, butylamino, and the like.

The term "dialkylamino" as used herein refers to $R_7R_8N-$ wherein $R_7$ and $R_8$ are independently selected from loweralkyl, for example diethylamino, methyl propylamino, and the like.

The term "alkenyl" as used herein refers to a branched or straight hydrocarbon chain comprising two to twenty carbon atoms, preferably four to twelve carbon atoms, especially about eight to ten carbon atoms, which also comprises one or more carbon—carbon double bonds, preferably about one to three double bonds. The exact number of double bonds, in part, depends on the length of the alkenyl radical. Double bonds are typically separated by at least one single bond and exist in either a cis or trans configuration. Compounds of the invention may either have a known configuration or may exist as a mixture of isomers. Variations in these parameters, i.e., number of double bonds and cis or trans configuration, result in a wide variety of compounds, all of which are encompassed by the invention. Representative alkenyl groups include, but are not limited to, trans,cis-1,3-nonadienyl; trans,cis,trans-1,3,6-nonatrienyl; trans,trans-1,2-nonadienyl; 2-propenyl (i.e., allyl); 3-methyl-2-butenyl; 3,7-dimethyl-2,6-octadienyl; 4,8-dimethyl-3,7-nonadienyl; 3,7,11-trimethyl-2,6,10-dodecatrienyl and the like.

The term "alkenyloxy" as used herein refers to a branched or straight hydrocarbon chain comprising two to twelve carbon atoms which also comprises one or more carbon—carbon double bonds which is linked to the parent molecular moiety through an oxygen atom. Representative alkenyloxy groups include 2-propenyloxy (i.e., allyl) and the like.

The term "alkoxy" or "lower alkoxy" as used herein refers to $R^*O-$ wherein $R^*$ is a loweralkyl group, as defined above. Alkoxy may also be represented as $C_n-C_m$-alkoxy where n and m respectively represent the minimum and maximum number of carbon atoms in the alkoxy radical. Examples of alkoxy include, but are not limited to, methoxy, ethoxy, propoxy, isopropoxy, n-butyloxy, tert-butoxy, and the like.

The term "aryl" as used herein refers to a mono-, fused bicyclic or fused tricyclic carbocyclic ring system having one or more aromatic rings including, but not limited to, phenyl, naphthyl, tetrahydronaphthyl, phenanthrenyl, biphenylenyl, indanyl, indenyl and the like. The term "bicyclic aryl" as used herein includes naphthyl, tetrahydronaphthyl, indanyl, indenyl and the like. The term "tricyclic aryl" as used herein includes anthracenyl, phenanthrenyl, biphenylenyl, fluorenyl, and the like. Aryl groups (including bicyclic and tricyclic aryl groups) can be unsubstituted or substituted with one, two or three substituents independently selected from loweralkyl, haloalkyl, alkoxy, thioalkoxy, amino, alkylamino, dialkylamino, alkenyloxy, hydroxy, halo, mercapto, nitro, carboxaldehyde, carboxy, alkoxycarbonyl and carboxamide. Substituents also include methylenedioxy and ethylenedioxy. In addition, substituted aryl groups include tetrafluorophenyl and pentafluorophenyl.

The term "aryl-aryl-" as used herein refers to two aryl groups which are the same or different linked by a covalent bond. Examples of aryl-aryl- include, but are not limited to, biphenyl, 4-(1-naphthyl)phenyl, 4-(2-naphthyl)phenyl, 4-phenylnaphth-1-yl and the like. The covalent linking bonds in aryl-aryl- are preferably para, i.e. 1,4-; and the preferred aryl-aryl-group is biphenyl.

The term "aryl-aryl-aryl-" as used herein refers to three aryl groups which are the same or different linked to each other by covalent bonds. Examples of aryl-aryl-aryl- include, but are not limited to, 4-(biphenyl)phenyl, 4-(biphenyl)naphth-1-yl, 6-(biphenyl)naphth-2-yl and the like. The covalent linking bonds in aryl-aryl-aryl- are preferably para, i.e. 1,4-; and the preferred aryl-aryl-aryl- group is 4-(biphenyl)phenyl.

The term "arylalkyl" as used herein refers to an aryl group as previously defined, appended to a loweralkyl radical, for example, benzyl and the like.

The term "arylalkenyl" as used herein refers to an aryl group as previously defined, appended to a lower alkenyl radical, for example, cinnamyl and the like.

The term "arylalkoxy" as used herein refers to an aryl group as previously defined, appended to a lower alkoxy radical, for example, benzyloxy, 1-naphthylmethoxy and the like.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, morpholinyl, alkenylmorpholinyl, and the like.

The term "hydroxy-protecting group" or "O-protecting group" as used herein refers to a removable substituent which protects hydroxyl groups against undesirable reactions during synthetic procedures such as those O-protecting groups disclosed in T. H. Greene and P. G. M. Wuts, "Protective Groups in Organic Synthesis", 2nd edition, John Wiley & Sons, New York (1991), which is incorporated herein by reference. O-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, triethylsilyl, t-butyldimethylsilyl and t-butyldiphenylsilyl; and esters prepared by reacting the hydroxyl group with a carboxylic acid, for example, acetate, propionate, benzoate and the like.

The term "hydroxy-protecting reagent" as used herein refers to those reagents which react with the hydroxy functionality to give the hydroxy protecting groups described above. For example, the hydroxy-protecting reagent triethylsilyl triflate affords the triethylsilyl hydroxy-protecting group. These reagents are described in Greene and Wuts, "Protective Groups In Organic Synthesis," 2nd edition, John Wiley & Sons, New York (1991). to those carboxylate salts, esters, and prodrugs of the compound of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. Pharmaceutically acceptable salts are well known in the art and refer to the relatively non-toxic, inorganic and organic acid addition salts of the compound of the present invention. For example, S. M. Berge, et al. describe pharmaceutically acceptable salts in detail in *J. Pharmaceutical Sciences,* 66: 1–19

(1977) which is incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Examples of pharmaceutically acceptable, non-toxic esters of the compounds of this invention include $C_1$ to $C_6$ alkanoyl esters wherein the alkanoyl group is a straight or branched chain. Esters of the compounds of the present invention may be prepared according to conventional methods.

The term "pharmaceutically acceptable prodrugs" as used herein refers to those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems,* Vol. 14 of the A.C.S. Symposium Series, and in Edward B. Roche, ed., *Bioreversible Carriers in Drug Design,* American Pharmaceutical Association and Pergamon Press, 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexyl-carbodiimide) method, the active ester method (p-nitrophenyl ester method, N-hydroxy-succinic acid imide ester method, cyanomethyl ester method and the like), the Woodward reagent K method, the DCC-HOBT (1-hydroxy-benzotriazole) method and the like. Classical methods for amino acid condensation reactions are described in M. Bodansky, Y. S. Klausner and M. A. Ondetti, *Peptide Synthesis,* Second Edition, NY, 1976, which is incorporated herein by reference.

Asymmetric centers may exist in the compounds of the present invention. Cis and trans isomers may also exist in the compounds of the present invention. Except where otherwise noted, the present invention contemplates the various stereoisomers, cis and trans isomers and mixtures thereof.

Preferred Embodiments

The present invention relates to a compound represented by the formula I:

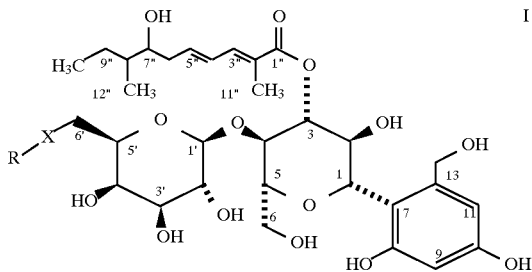

as well as a pharmaceutically acceptable salt, ester of prodrug thereof. In the above formula:

R is:

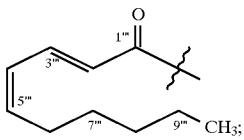

—C(O)—$R_1$ wherein $R_1$ is alkyl, alkenyl, aryl, arylalkenyl, aryl-aryl-, arylalkoxy-aryl-, aryl-aryl-aryl-, arylkoxy-aryl-aryl-, or

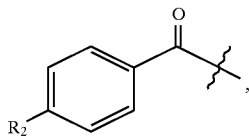

wherein $R_2$ is alkylamino, dialkylamino, (heterocyclic) alkyl, aryl, or arylalkyl; and X is O, NH, or $NR_3$ wherein $R_3$ is alkyl or aryl.

A preferred embodiment of the present invention is a compound of Formula I, wherein X is O; and R is —C(O)—$R_1$ wherein $R_1$ is alkenyl, aryl, arylalkyl, aryl-phenyl-, arylalkoxy-phenyl-, aryloxy-phenyl-, aryl-aryl-phenyl- or arylalkoxy-aryl-phenyl-; and X is O; or a pharmaceutically acceptable acid, ester or prodrug thereof.

A more preferred embodiment of the present invention is a compound of Formula I wherein X is O; and R is —C(O)—$R_1$ where $R_1$ is an alkenyl groups containing 10 or fewer carbon atoms and two and three double bonds, phenyl, naphthyl, anthracenyl, phenanthrenyl, biphenylenyl, styryl, benzyl, naphthylmethyl, biphenyl, naphthyl-phenyl-, phenyl-naphthyl-, or biphenyl-phenyl-, wherein phenyl or aryl groups are unsubstituted or substituted with one or two groups selected from $C_1$–$C_5$-alkyl, allyloxy, $C_1$–$C_8$-alkoxy, methylenedioxy, and hydroxy.

An even more preferred embodiment of the present invention is a compound of Formula I wherein X is O; and R is —C(O)—$R_1$ wherein $R_1$ is phenanthrenyl, unsubstituted biphenyl or biphenyl substituted with $C_1$–$C_3$-alkyl or $C_1$–$C_3$-alkoxy.

The most preferred embodiment of the invention is a compound of Formula I, wherein X is O; and R is a radical of the formula:

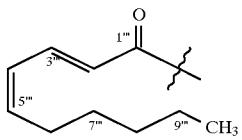

in which instance the compound is designated Corynecandin.

The compounds of the invention exhibit in vitro activity as antifungal agents against a variety of fungal organisms and inhibit (1,3)-β-glucan synthase. They are therefore expected to be useful in the treatment of fungal infections in mammals. When used in such treatment, a therapeutically effective amount of the compound of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat the targeted disorder, at a reasonable benefit/risk ratio applicable to any medical treatment, which is administered in such quantities and over such a period of time as is necessary to obtain the desired therapeutic effect. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compound of this invention administered to a human or lower animal may range from about 0.1 to about 100 mg/kg/day or for topical administration from about 0.1 to about 10% in cream, ointment or other topical formulation or for rectal or vaginal administration from about 10 to about 500 mg per dose in a suitable vehicle. For purposes of oral administration, doses may be in the range of from about 1 to about 100 mg/kg/day or, more preferably, of from about 10 to about 20 mg/kg/day. If desired, the effective daily dose may be divided into multiple doses for purposes of administration; consequently, single dose compositions may contain such amounts or submultiples thereof as make up the daily dose.

The pharmaceutical compositions of the present invention comprise a compound of the invention and a pharmaceutically acceptable carrier or excipient, which may be administered orally, rectally, parenterally, intracisternally, intravaginally, intraperitoneally, topically (as by powders, ointments, or drops), bucally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection include pharmaceutically acceptable sterile nonaqueous solutions or aqueous dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose and acacia, c) humectants such as glycerol, d) disintegrating agents such as agar—agar, calcium carbonate, potato or tapioca starch, alginic acid, certain silicates and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols and sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, olive, castor and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, and sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

The compound of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology,* Volume XIV, Academic Press, New York, N.Y., 1976, p. 33 et seq.

The compounds of the present invention may be produced by culturing, in appropriate media, fungal microorganisms which are capable of producing corynecandin. The compounds are produced when the culture is grown in a stationary or submerged fermentation with a culture medium containing a source of carbon and a source of nitrogen. Media which are useful include an assimilable source of carbon such as starch, sugar, molasses, glycerol, a combination of glucose plus molasses, etc.; an assimilable source of nitrogen such as protein, protein hydrolysate, polypeptides, amino acids, peptone plus yeast extract or whole yeast, etc.; and other optional organic and inorganic ingredients which can be added to stimulate production of the corynecandin compounds. For example, inorganic anions and cations including potassium, magnesium, calcium, ammonium, sulfate, carbonate, phosphate, chloride, etc. may be added to the medium. Further, buffers such as calcium carbonate can be added to aid in controlling the pH of the fermentation medium. The stationary fermentation may include a solid support to increase the surface area available for fungal growth. Suitable supports include Shredded Wheat Spoon Size®, rolled oats, barley, cracked corn, rice, millet, corn bran, wheat bran, oat bran, vermiculite, etc. The culture may be incubated in stationary vessel (without movement) or in a cylindrical or other vessel which is rolled or agitated to increase aeration. A preferable method is a liquid, submerged, agitated culture process are feasible. In these cases, aeration may be provided by forcing sterile air through the fermentation medium. Agitation can be provided by shaking the container or by stirring the culture, for example, with a mechanical stirrer. The fermentation is generally carried out in a temperature range of from about 15° C. to about 35° C. The pH of the fermentation is preferably maintained between 3 and 9. The compound is produced and accumulated between 3 and 28 days after inoculation of the fermentation medium.

Subsequent to the fermentation process, the corynecandin compound can be extracted from the fermentation broth as for example with ethyl acetate/acetone solvent mixtures. Partial purification of the active components can be achieved by sequential trituration of the organic extract with organic solvents such as ethyl acetate, ethanol and methanol in order to selectively remove the desired organic compounds. The extracts may be further purified by use of various partitioning solvent systems such as, for example, chloroform/methanol/water, hexane/ethyl acetate/methanol/water, or ethanol/ethyl acetate/water. Further purification and separation of individual components can be achieved by countercurrent chromatography in solvent systems such as, for example, ethyl acetate/ ethanol/water, chloroform/methanol/water, or chloroform/carbon tetrachloride/methanol/water, and/or by adsorption onto silica gel and subsequent elution with organic solvents and solvent mixtures such as ethyl acetate, chloroform and methanol. Size exclusion chromatography on resin such as SEPHADEX® LH-20, developed in a solvent such as methanol, affords the pure compound.

The processes useful in the preparation of the above compounds are represented in Schemes I and II.

In Scheme I, corynecandin (1) is treated with an hydroxy protecting reagent (for example, triethylsilyl triflate or trimethylsilyl triflate or triethylsilyl chloride or trimethylsilyl chloride) to give the protected corynecandin derivative 2 (wherein R' is an hydroxy protecting group). Reduction of the ester functionality (for example, using a reducing reagent such as diisobutyl aluminum hydride or lithium aluminum hydride or selectrides and the like) at the 6'-position of compound 2 affords the 6'-alcohol compound 3. The hydroxymethyl functionality is acylated (for example, using an acid chloride or an acid anhydride) to give the 6'-acyl compound 4 (wherein R is as defined above herein). Alternatively, the hydroxymethyl functionality may be reacted with a carboxylic acid compound in the presence of 4-dimethylaminopyridine and a coupling reagent such as dicyclohexylcarbodiimide to give compound 4.

The acid chlorides, anhydrides and carboxylic acids (R—C(O)—Cl, R—C(O)—O—C(O)—R and R—CO₂H respectively) are either commercially available or readily prepared using organic synthesis methods known in the art.

The hydroxy protecting groups are removed (for example, using HF in acetonitrile or tetrabutylammonium fluoride in TBF or acetic acid and the like) to give the desired compound 5.

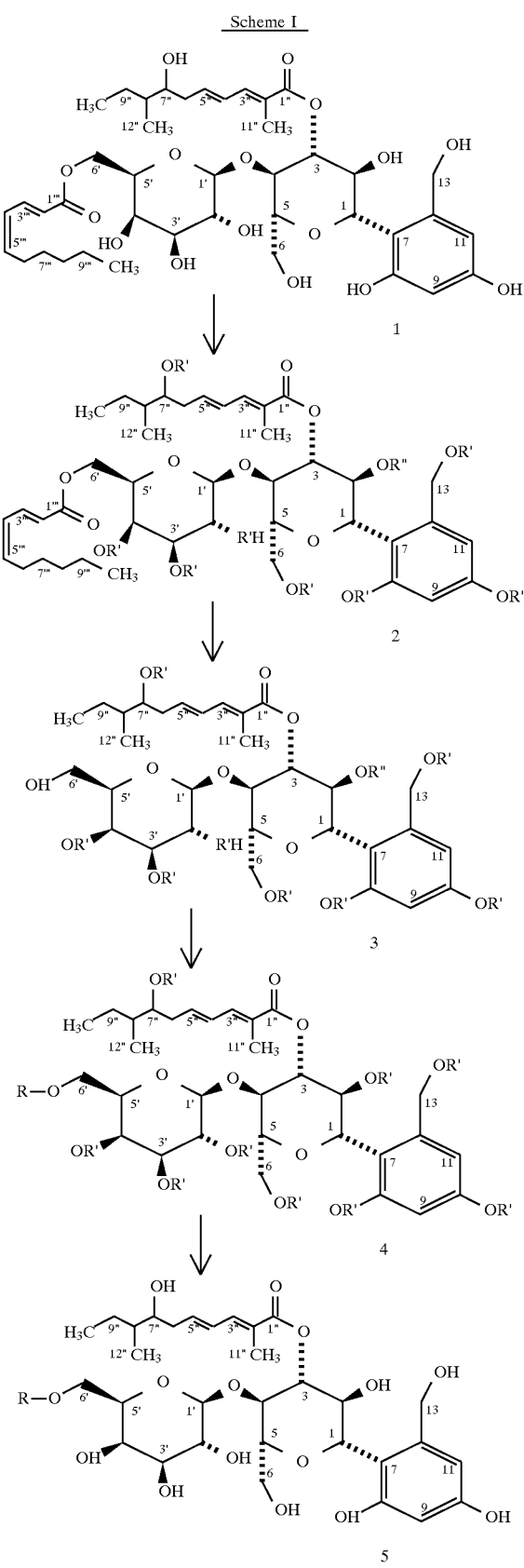

In a preferred embodiment shown in Scheme II, corynecandin (1) is treated with triethylsilyl (TES) triflate in collidine to give the TES-protected corynecandin derivative (6). Reduction of the ester functionality using diisobutyl aluminum hydride affords the 6'-hydroxymethyl compound 7). The hydroxymethyl functionality is acylated (for example, using an acid chloride or an acid anhydride) to give compound 8. The hydroxy protecting groups are removed (for example, using HF in acetonitrile or tetrabutylammonium fluoride in THF) to give the desired compound 9.

Scheme II

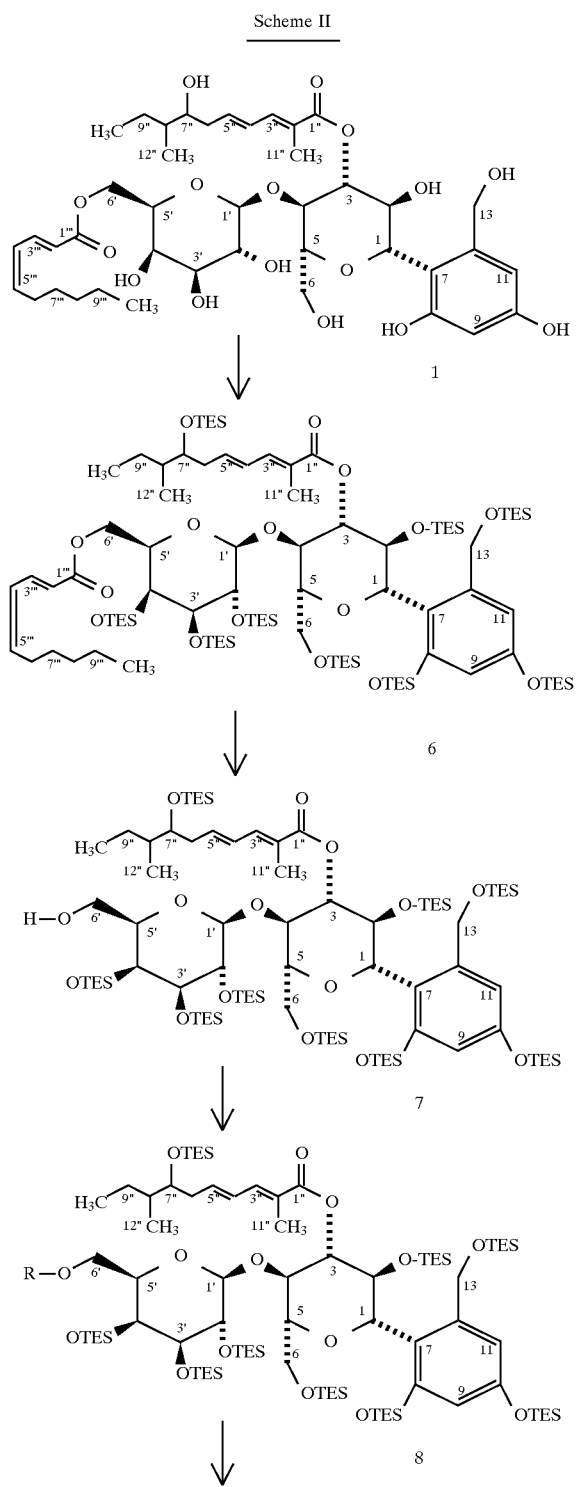

-continued
Scheme II

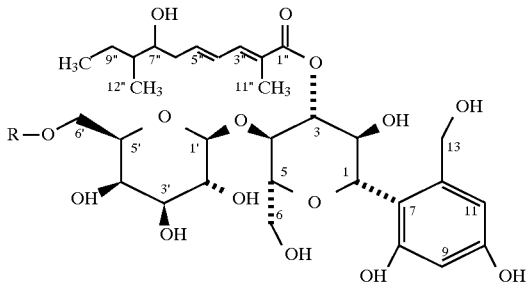

9

The compounds, processes and uses of the present invention will be better understood in connection with the following examples, which are intended as an illustration of and not a limitation upon the scope of the invention. The following abbreviations were used: EtOAc for ethyl acetate, EtOH for ethanol, MeOH for methanol, THF for tetrahydrofuran and TLC for thin layer chromatography.

EXAMPLE 1

Identification and Characterization of the Corynecandin-Producing Strain *Coryneum modonium* species AB 2020T-223 (NRRL 25349)

The compounds of the present invention, "corynecandins", were first obtained from a fungus isolated from the plant *Tradescantia osarkana* which was collected south of Jasper in Newton County, Arkansas, U.S.A. The culture, which was designated strain AB 2020T-223, a *Coryneum modonium* species as indicated by the production of characteristic macroconidia. A subculture of this microorganism was deposited in the permanent collection of the National Center for Agricultural Utilization Research, United States Department of Agriculture, 1815 North University Street, Peoria, Ill. 61604, U.S.A., under the terms of the Budapest Treaty, and accorded accession number NRRL 25349. All the restrictions on the availability of the culture required for the manufacture of the claimed compound will be removed upon the issuance of a patent maturing from the present application.

Strain AB 2020T-223 was identified at the University of Alberta Microfungus Collection and Herbarium. Colonies of strain AB 2020T-223 attained a diameter of 25–28 mm when grown on Potato Dextrose Agar (Difco) for 14 days at 25° C. in the dark. The colonies had a felty texture, were raised but had a depressed center. The codes in parenthesis following the color names in the colony description that follows are Munsell color notations from The Munsell Book of Color, Glossy Finish Collection, Macbeth Division of Kollmorgen Instruments Corporation, New Windsor, N.Y., 1994. The color names are taken from Kelly, K. L. & D. B. Judd: Color: Universal Language and Dictionary of Names, pp 15–39, U.S. National Bureau of Standards, Special Publication 440, U.S. Government Printing Office, Washington, D.C., 1976. They were colored grayish purple (5P 4/2) with a yellowish gray (7.5Y 8/2) edge and formed a light yellow (5Y 8.5/8) soluble pigment. No exudate was produced. The colony reverse was colored moderate olive (5Y 4/4). Although no fruiting bodies were observed at 14 days, the culture formed characteristic large spores with age. The conidia were variable but typically measured 13–16×

43–73 μm. They were clavate or fusiform, straight or slightly curved and 5–8 distoseptate.

EXAMPLE 2

Growth of *Coryneum modonium* species AB 2020T-223 in Submerged Culture

The active compound was produced by fermentation in a 42-liter LH Fermentation stainless steel stirred vessel. *Coryneum modonium* AB 2020T-223 was maintained as frozen vegetative mycelium at −75° C. Inoculum for fermentation was prepared in two stages to help overcome the slow growth of this fungus. The seed medium consisted of soybean meal 2%, glucose monohydrate 3%, $CaCO_3$ 0.6%, NaCl 0.3%, $NH_4Cl$ 0.25% and $KH_2PO_4$ 0.2%. For the first stage, 100 ml of the seed medium contained in 500 ml Erlenmeyer flasks was inoculated at 3% with the vegetative stock and incubated at 28° C. for 3 days. For the second stage, 600 ml of the same seed medium was sterilized in 2-liter Erlenmeyer flasks. These were inoculated at 5% with first stage growth and incubated at 28° C. for 3 days. The fermentor was charged with 30 liters of a medium consisting of soybean meal 1.5%, beef extract 0.3%, casamino acids 0.5%, soluble starch 1%, maltose 1%, dextrin 1% and $CaCO_3$ 0.4%. The medium was prepared in deionized water and the pH was 6.5. Sterilization was at 121° C. and 15 psi for 1 hour. The second stage seed was used at 5% to inoculate the fermentor. Fermentation was carried out at 25° C. for 10 days. The agitation was 350 rpm, the aeration was 1.0 vol/vol/min and the head pressure was 15 psi.

EXAMPLE 3

Isolation of Corynecandin from Submerged Culture

The mycelial mass was filtered and extracted with acetone (41) followed by methanol (41). The combined extracts were concentrated to give a brown gum (70 g) which was triturated with hexane (3×300 ml) and $CH_2Cl_2$ (3×300 ml) respectively. The evaporation of the active $CH_2Cl_2$ triturate produced a brown gum (2.7 g). The active compound was isolated by countercurrent chromatography of a portion of the $CH_2Cl_2$ triturate (0.3 g) using the upper organic layer from toluene-EtOAc-MeOH-water (0.5:5:2:3) system as the mobile phase (2 ml/min) on a Sanki LLB-M CPC instrument at 1200 rpm and 7 ml fractions were collected. The active fractions, 11 to 13, were pooled and the solvent was removed to give the active compound corynecandin (3 mg) as an amorphous powder.

EXAMPLE 4

Physico-Chemical Characterization of Corynecandin

The structure elucidation of the active compound (λ268.5 nm, ε=32,000; HRFAB-MS m/z 809.3972 (M+H⁺ $C_{41}H_{60}O_{16}$, Δ1.6 ppm)) was carried out using a combination of 2D Nuclear Magnetic Resonance (NMR) methods such as DEPT, COSY, HMQC, HMBC, and ROESY experiments and MS/MS studies. The NMR data of corynecandin in $CD_3OD$ are set forth in Table 1 below.

TABLE 1

| C # | ¹³C shift/ppm | 1H shift/ppm[a] | $J_{HH}$/Hz | long-range H-C correlations[b] |
|---|---|---|---|---|
| 1 | 78.7 | 4.8 | d, 10.1 | 2, 3, 7, 8, 12 |
| 2 | 72.1 | 4.15 | dd, 10.1, 9.3 | 1, 4 |
| 3 | 79.2 | 5.2 | dd, 9.3, 9.3 | 2, 4, 1" |
| 4 | 77.1 | 4.05 | dd, 9.3, 9.5 | 3, 5, 6, 1' |
| 5 | 81.5 | 3.62 | m | 4, 6, 1' |
| 6 | 61.1 | 3.88 | d, 12.0 | 5 |
|   |   | 4.18 | dd, 12, 2.0 | 5 |
| 7 | 114.5 |   |   |   |
| 8 | 158.7 |   |   |   |
| 9 | 104.5 | 6.28 | d, 2.4 | 7, 8, 10, 11 |
| 10 | 159.3 |   |   |   |
| 11 | 109.4 | 6.4 | d, 2.4 | 7, 9, 10, 12, 13 |
| 12 | 143.1 |   |   |   |
| 13 | 63.7 | 4.54 | d, 12.3 | 7, 8, 11 |
|   |   | 4.62 | d, 12.3 | 7, 8, 11 |
| 1' | 105.2 | 4.35 | d, 7.3 | 4 |
| 2' | 74.7 | 3.4 | m | 1', 3' |
| 3' | 72.6 | 3.45 | m | 2', 5' |
| 4' | 70 | 3.75 | dd, 3.0, 1.1 | 2', 3', 6' |
| 5' | 73.8 | 3.63 | m | 4', 6' |
| 6' | 64.1 | 4.1 | dd, 11.1, 6.0 | 4', 5', 1''' |
|   |   | 4.2 | dd, 11.1, 7.0 | 4', 5', 1''' |
| 1" | 170.1 |   |   |   |
| 2" | 126.9 |   |   |   |
| 3" | 140 | 7.25 | dq, 11.3, 1.1 | 1", 5", 11" |
| 4" | 129 | 6.45 | dd, 11.3, 15.0 | 2", 3", 6" |
| 5" | 141.4 | 6.15 | dm, 15.0 | 3", 6", 7" |
| 6" | 39.6 | 2.35 | m | 4", 5", 7", 8" |
| 7" | 75 | 3.55 | m | 12" |
| 8" | 41.2 | 1.38 | m |   |
| 9" | 27.1 | 1.2 | m |   |
|   |   | 1.5 | m |   |
| 10" | 12.2 | 0.8 | t, 7.0 | 8", 9" |
| 11" | 13.1 | 1.95 | d, 1.1 | 1", 2", 3" |
| 12" | 13.8 | 0.85 | d, 2.7 |   |
| 1''' | 168.5 |   |   |   |
| 2''' | 121.7 | 5.9 | d, 14.9 | 1''', 3''', 4''' |
| 3''' | 141.4 | 7.65 | ddd, 14.9, 11.6, 1.1 | 1''', 4''' |
| 4''' | 127.5 | 6.2 | ddm, 11.6, 10.1 | 2''', 6''' |
| 5''' | 143.3 | 5.95 | dd, 10.1, 6 | 3''', 4''' |
| 6''' | 29.2 | 2.3 | m | 7''', 8''' |
| 7''' | 30.1 | 1.4 | m |   |
| 8''' | 32.5 | 1.15 | m |   |
| 9''' | 23.5 | 1.05 | m |   |
| 10''' | 14.4 | 0.89 | t, 7.0 | 8''', 9''' | a) Assigned by HMQC, b) Observed by HMBC

The signals for all 41 carbons were identified by a DEPT experiment and 51 attached protons could be accounted for. The structure of compound of formula I differs from that of chaetiacandin in having a shorter ester chain at C3. The long range H-C connectivities of the two meta coupled aromatic protons signals at 6.4 and 6.28 ppm (d, J=2.4 Hz) allowed the identification of the aromatic moiety as 2-substituted-3,5-dihydroxybenzyl alcohol. A methine proton signal at 4.8 ppm (d, J=10.1 Hz, H1) showing long range H—C connectivities to carbon signals at 114.5 (C7), 158.7(8), and 143.1 (C12) was identified as due to the pseudo-anomeric proton of a C-glycoside attached to the aromatic moiety. The spin system for the C-glycosidic sugar continued sequentially through the methine proton signals at 4.15 (dd, J=10.1, 9 Hz, H2), 5.2 (dd, J=9.3, 9.3 Hz, H3), 4.05 (dd, J=9.5, 9.3, H4) and 3.62 ppm (m, H5); and ended at the methylene proton signals at 3.88 and 4.18 ppm (dd, J=12.2, 2 Hz, $H_2$6). The large coupling and the presence of NOE interactions between signals for protons at C1, C3, and C5 suggested that all protons assume axial conformations and the C-glycoside was identified as having the same stereochemistry as glucose. The long range correlations observed between the proton and carbon signals at 5.2 ppm and 170.1 ppm (C1")

and 4.01 ppm and 105.2 ppm (C1') allowed, respectively, the placement of an ester function on C3 and an O-glycoside on C4 of this unit. The proton spin system of the second sugar included sequentially the methine proton signals at 4.35 (d, J=7.3 Hz, H1'), 3.45 (m, H2'), 3.4 (m, H3'), 3.75 (dd, J=3, 1.1 Hz, H4') and 3.63 ppm (m, H5'); and terminated with the methylene proton signals at 4.1 and 4.2 ppm (dd, 11.1, 7 Hz, H$_2$6'). The large coupling between H1' and H2' and the presence of NOE interactions between H1', H3', and H5' were indicative of the axial conformation of all 4 protons while the smaller coupling of the signal at 3.75 ppm indicated the equatorial conformation of the proton at C4'. Therefore the relative stereochemistry of the second sugar unit was that of galactose. The long range coupling between the methylene proton signals and the carbon signal at 168.5 ppm indicated the presence of a second ester function on C6'. The two aliphatic acid chains were identified by the analyses of 2D nmr data and the configuration of the olefinic bonds were assigned based on NOE experiments: strong NOE effects were observed between signals at 6.15 and 7.25 ppm and between signal at 6.45 and 1.95 ppm indicating trans-trans configuration for the 2", 4" diene. Similarly the NOE effects between signals at 5.9, 6.2, and 5.95 ppm suggested a transcis configuration for the 2'", 4'" diene.

The proposed structure of the compound of Formula I was determined by FAB MS/MS. Product ion spectra were obtained using linked-scanning at constant B/E on a JEOL SX102A mass spectrometer. Fragmentation of the [M+Na]+(m/z 831) precursor ion resulted from CID using helium collision gas. All m/z values shown are for natriated productions. The fragmentation pattern is shown in Formula II below.

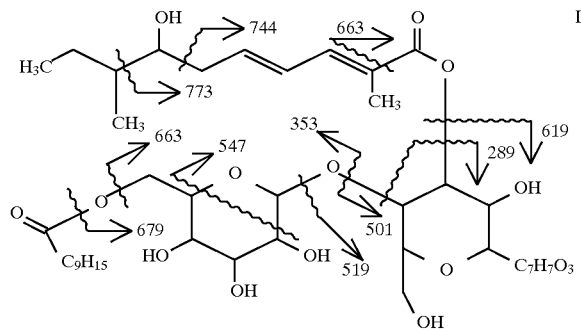

II

In Vitro Assay of Antifungal Activity

Minimal inhibitory concentrations (MICs) of corynecandin related compounds in the microtiter broth dilution in the presence and absence of 0.8M sorbitol assay were determined by a broth dilution assay described by Frost, D., Brandt, K., Cugier, D., and Goldman, R. in *J. Antibiotics* 48: 306–310 (1995), which is incorporated herein by reference. The MIC for corynecandin compounds is compared with those for the other compounds listed in Table 2 below.

TABLE 2

| | Broth Dilution Assay[a] MIC at 2 day growth (mg/ml) | |
|---|---|---|
| Compound | w/o sorbitol | with sorbitol |
| Corynecandin | 0.98 | >250 |
| Fusacandin | 1.96 | >250 |
| Papulacandin B | 1.96 | >250 |

TABLE 2-continued

| | Broth Dilution Assay[a] MIC at 2 day growth (mg/ml) | |
|---|---|---|
| Compound | w/o sorbitol | with sorbitol |
| Cilofungin | 0.98 | >250 |
| Amphotericin B | 0.48 | >250 |

[a]Assay conducted as described in Frost et al., ibid, except final concentration of cells was 2 × 10$^5$ organisms/ml.

In Vitro Inhibition of (1,3)-β-Glucan Synthase Activity

The fungal cell wall serves as a protective barrier and is essential for viability in a hypotonic environment. (1,3)-β-Glucan is a component of the *Candida albicans* cell wall, and the enzyme that biosynthesizes this polymer, glucan synthase, is not present in higher eukaryotes. (Glucan synthase is an integral plasma membrane protein that catalyzes polymerization of uridine diphosphate-glucose (UDP-Glc) into β-glucan.) Accordingly, glucan synthase represents an ideal target for the development of antifungal agents.

The assay was conducted as described by Frost, D., Brandt, K. Capobioanco, and Goldman, R., *Microbiology* 140: 2239–2246 (1994) which is incorporated herein by reference. The results are shown in Table 3.

TABLE 3

| In Vitro Inhibition of (1,3)-β-Glucan Synthase Activity IC$_{50}$ (μg/mL) | |
|---|---|
| Compound | IC$_{50}$ (μg/mL) |
| Corynecandin | 12.9 |
| Fusacandin | 25.0 |
| Papulacandin | 1.9 |
| Cilofungin | 52.0 |
| Amphotericin B | ND |

Corynecandin was found to have similar potency as an antifungal agent to several other papulacandin-type compounds (Table 3). Sorbitol could rescue the growth of cells when treated with corynecandin indicating that this compound also inhibits fungal cell wall synthesis and assembly. The ester chain found at C3 is not found in other glycolipids and corynecandin is the smallest known member of this class to retain antifungal and glucan synthase inhibitory activity.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art, and may be made without departing from the spirit and scope thereof.

What is claimed is:

1. A compound having the formula

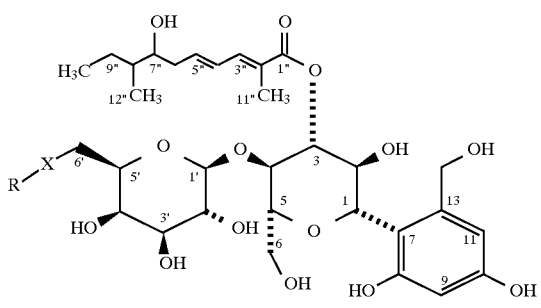

as well as a pharmaceutically acceptable salt, ester of prodrug thereof, wherein R is:

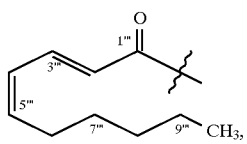

—C(O)—$R_1$ wherein $R_1$ is alkyl, alkenyl, aryl, arylalkenyl, aryl-aryl-, arylalkoxy-aryl-, aryl-aryl-aryl-, arylkoxy-aryl-aryl-, or

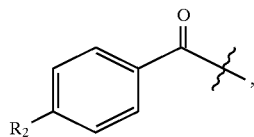

wherein $R_2$ is alkylamino, dialkylamino, (heterocyclic) alkyl, aryl, or arylalkyl; and X is O, NH, or $NR_3$ wherein $R_3$ is alkyl or aryl;

or a pharmaceutically acceptable acid, ester or prodrug thereof.

2. A compound according to claim 1 wherein X is O; and R is —C(O)—$R_1$, wherein $R_1$ is alkenyl, aryl, arylalkyl, aryl-phenyl-, arylalkoxy-phenyl-, aryloxy-phenyl-, aryl-aryl-phenyl- or arylalkoxy-aryl-phenyl-.

3. A compound according to claim 1 wherein X is O; and R is —C(O)—$R_1$ wherein $R_1$ is $C_2$–$C_{12}$-alkenyl groups containing up to three double bonds, $C_2$–$C_{12}$-alkyl, phenyl, naphthyl, anthracenyl, phenanthrenyl, biphenylenyl, styryl, benzyl, naphthylmethyl, biphenyl, naphthyl-phenyl-, phenyl-naphthyl-, biphenyl-phenyl-, wherein phenyl or aryl groups are unsubstituted or substituted with one or two groups selected from $C_1$–$C_5$-alkyl, allyloxy, $C_1$–$C_8$-alkoxy, methylenedioxy, and hydroxy.

4. A compound according to claim 1 wherein X is O; and R is

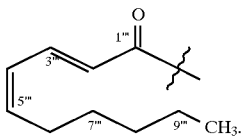

5. A pharmaceutical composition comprising a compound according to claim 1 in combination with a pharmaceutically acceptable carrier.

6. A pharmaceutical composition comprising a compound according to claim 4 in combination with a pharmaceutically acceptable carrier.

7. A method of treating a fungal infection in a patient in need of such treatment, comprising administering to the patient a therapeutically effective amount of a compound according to claim 1.

8. A method of treating a fungal infection in a patient in need of such treatment, comprising administering to the patient a therapeutically effective amount of a compound according to claim 4.

9. A process for preparing a compound according to claim 1, comprising the steps of
   (a) culturing a microorganism having substantially all the characteristics of *Coryneum modonium* AB 2020T-223 under suitable conditions in a fermentation medium containing assimilable sources of carbon and nitrogen;
   (b) allowing the compound to accumulate in the fermentation medium; and
   (c) isolating the compound from the fermentation medium.

10. A process according to claim 9 wherein the microorganism is *Coryneum modonium* strain NRRL 25349 or a mutant or derivative thereof.

* * * * *